United States Patent
McManus

(12) 
(10) Patent No.: US 6,187,728 B1
(45) Date of Patent: Feb. 13, 2001

(54) SOLID PERSONAL CARE COMPOSITION HAVING FOAMED POLYMER SKIN AND SHAPE OF A FRUIT OR VEGETABLE

(75) Inventor: Marjorie McManus, Bloomfield, NJ (US)

(73) Assignee: Dragoco Gerberding & Co. AG (DE)

( * ) Notice: Under 35 U.S.C. 154(b), the term of this patent shall be extended for 0 days.

(21) Appl. No.: 09/306,544

(22) Filed: May 6, 1999

(51) Int. Cl.[7] ....................................................... A61K 7/50
(52) U.S. Cl. ......................... 510/142; 510/146; 510/147; 510/151; 510/152
(58) Field of Search ................................... 510/141, 142, 510/143, 144, 146, 147, 151, 152

(56) References Cited

U.S. PATENT DOCUMENTS

| | | |
|---|---|---|
| 4,996,000 | 2/1991 | Redeker . |
| 5,221,506 | 6/1993 | Dulin . |
| 5,857,792 | 1/1999 | Iffinger . |

FOREIGN PATENT DOCUMENTS

| | | | |
|---|---|---|---|
| WO 94/12088 | 6/1994 | (WO) | ................................ A47K/7/03 |
| WO 97/24053 | 7/1997 | (WO) | ................................ A47K/7/02 |

*Primary Examiner*—Necholus Ogden
(74) *Attorney, Agent, or Firm*—Pendorf & Cutliff

(57) ABSTRACT

A composite article comprising a solid cosmetic formulation core, preferably of transparent glycerin soap, and a foamed polymer skin, preferably a sponge. The solid soap-core is preferably formulated to mimic the meat of a fruit such as an orange. The sponge-skin is preferably formulated to mimic the skin appropriate to the meat, for example, an orange peel. At least the meat and preferably also the skin part includes dyes and fragrances to impart the color and smell of the fruit being imitated. The composite article is produced either by forming the soap core, coating a sponge forming polymeric composition onto the soap core, and foaming and curing the coating to form a sponge skin on the soap core, or by first forming a hollow foamed polymer shell, introducing liquefied soap into the shell, and hardening the soap.

15 Claims, 2 Drawing Sheets

SOLID PERSONAL CARE COMPOSITION HAVING FOAMED POLYMER SKIN AND SHAPE OF A FRUIT OR VEGETABLE

BACKGROUND OF THE INVENTION

1. Field of the Invention

The present invention concerns a novel article for personal hygiene, and more particularly, a soap and sponge combination, and to a method for the simple and economical manufacture thereof. The soap is preferably generally spherical and coated with a foamed polymer, the combination giving the overall appearance of a fruit or vegetable with skin or peel. The coating not only serves as a potential sponge for cleaning, but functions as the "wrapper" that can be peeled off to reveal the soap.

2. Description of the Related Art

In the cleaning of human skin, soaps or detergents are used to provide an emulsifying action for dissolving dirt and keeping dirt away from the skin. However, in addition to this chemical action, a mechanical abrasive action is usually also required for the initial dislodging of dirt from the skin. Thus, in addition to the chemical action provided by soap, a mechanical element is required through which mild abrasive action can be imparted to the skin. This mechanical element is most often found in the form of a particulate abrasive such as pumice, or a material such as a cloth or a sponge.

Attempts have been made to provide a single article which provides both the chemical and mechanical actions. However, the articles available today require improvement.

For example, U.S. Pat. No. 4,996,000 (Redeker) entitled "Multilayer cleansing bar" teaches a cleansing bar having layers of different cleansing materials. Redeker teaches that two kinds of cleansing bars are known. Soap bars are used for cleaning delicate skin. Scouring bars, which in addition to containing soap may contain large percentages of abrasive materials such as diatomaceous earth, clay, finely powdered silica, or volcanic ash, are used to clean areas such as hands exposed to more hard-to-remove dirt and grease than the rest of the body. Redeker addresses the problem of the need for having different cleansing bars for the different needs, and solves the problem by providing a single bar with, for example, one side formulated as a solid soap and the other side formulated as a scouring bar.

For the general cleaning of the body, and particularly the face, cloths or sponges are preferred over scouring particles. However, soap must be constantly reapplied to the conventional cloth or sponge. Attempts have been made to overcome this problem by combining the soap and the cloth or sponge into a single article. However, a review of patent literature reveals that combination articles proposed thus far are mainly functional in their appearance, expensive in their manufacture, associated with a number of detracting structural features such as VELCRO strips, glue layers, etc., or so primitive that they could easily be manufacture at home, such as by sewing a wash-cloth into a pocket for receiving soap.

Thus, there is known, for example, the article disclosed in U.S. Pat. No. 4,457,640 (Anderson) entitled "Body wash pad for bathing". Anderson teaches a body wash pad for bathing, the pad being constructed of a decorative terry cloth outer casing and a water absorbent core, the casing having a terry cloth lined, closeable pocket for insertion of a bar of soap, the terry cloth lined pocket providing a moderate abrasive action. This article has a home-made look and feel.

Various combinations of soaps and sponges are known. U.S. Pat. No. 5,221,506 (Dulin) entitled "Bar soap with structural core" teaches a bar soap for personal use having a soap shell and a structural center selected from an open celled sponge material or organic filamentary material such as water soluble oxycellulose polymers. The sponge core is revealed after the soap bar is reduced to a sliver, thus providing structural support for the sliver of soap, preventing breakage, making washing more effective and reducing wastage when only a sliver of soap remains. In an alternative embodiment, the core may extend to one surface. Thus, even in this alternative embodiment, the amount of sponge available for scrubbing the skin varies with use, from no sponge available initially to all sponge and no soap at the end. Thus, for effective cleaning, a separate wash cloth or sponge is required at least initially. Further, the soap bar requires a wrapper when displayed at the retail level.

U.S. Pat. No. 5,857,792 (Iffinger) entitled "Apparatus for a bar of soap and attached sponge" teaches a bar of soap in combination with a sponge for use in washing a persons body. The bar of soap is either adhesively bonded to the sponge or mechanically bonded to a plate or substrate which is in turn adhesively bonded to the sponge. The specification does not teach adhesives or methods for adhesively bonding soap directly to the sponge. The specification teaches melting soap, pouring the molten soap onto the first side of a substrate having anchoring projections, solidifying the soap around the projections, and adhering a sponge to the second side of the substrate. Since the substrate layer (or adhesive layer) insulates the soap from the sponge, it is not seen how soap can be transferred to the sponge during use.

U.S. Pat. No. 4,457,643 (Caniglia) entitled "Sponge for containing soap" teaches a soap and sponge washing device, for example, for washing the body in a shower or bath. The device includes a container forming an envelope for a bar of soap, discrete openings through to the container interior allowing water access to the soap and the facile exiting of lather for washing purposes, and a tab-like locking strip integral with the container material for locking the soap in the container. The device looks home-made and would not excite the interest of consumers.

WIPO Publication WO94/12088 (Harsveld) entitled "A soap and sponge combination" teaches the combination of (1) a sponge having a cavity for receiving a bar of soap, (2) a bar of soap seated in the cavity, and (3) a second sponge for capping the cavity after introduction of soap and secured by, e.g., VELCRO or other means. Again, the device is functional, home-made in appearance, and uninspiring.

WIPO Publication WO9724053 (Milo et al) teaches a washing system which comprises a cleansing agent and a separate reticulated sponge material. The sponge is preferably made of a synthetic polymer, preferably metallocene polyethylene, but may be polyurethane, polyester, polyethylene, polyether, polyester based urethane, base urethane, polyvinyl alcohol, and polyolefins such as polypropylene, silicate foams, ceramic foams, latex foams, and natural rubber foams and cellulose sponges. The cleansing agent is provided separately from the sponge, and is placed on the skin or on the sponge prior to scrubbing the skin.

Recently, U.S. Pat. No. 5,857,794 (Chien) entitled "Structure of bathing container" issued disclosing a bathing soap container having two pouches spaced for the allocation of soap, a sponge or rubbing balls. The inner space is arranged to hold a sponge or rubbing balls while the mouth of the first pouch portion may be folded over to accommodate a smaller sized soap. Even though this patent is recent, the device appears primitive and homemade.

Separately from the above, there has been an increasing trend to make the bathing experience more relaxing and luxurious. This has been done in part by making shower gels and shampoos more herbal or floral. However, other than enhancing the natural fragrances, the product remains primitive in appearance, the physical form having remained unaltered.

There is a need for a revolutionary new product that solves the problems inherent in the soap art. The new product should have a unique appearance, should provide an attractive merchandising display, and should provide the bather with a new bathing experience.

SUMMARY OF THE INVENTION

Broadly, these and other objects of the present invention have been accomplished by providing a composite product comprising a soap core, preferably of transparent glycerin soap, and a sponge skin. In contrast to the above articles wherein soap and sponge are formed separately and combined in a subsequent step, the article of the present invention is formed by intimately contacting the soap and skin during the formation of either the soap core or sponge skin, resulting in an intimate, seamless article requiring no VELCRO-strips, snap fasteners, etc. Depending upon the selected combination of materials, the soap and foamed skin can be chemically fused or mechanically engaged, but in embodiments wherein a whole skin completely encompasses the soap core, no bonding of sponge to soap is necessary.

The solid soap-core is preferably formulated to mimic the meat of a fruit such as an orange. The sponge-skin is preferably formulated to mimic the skin appropriate to the meat, for example, an orange peel. Both the meat and skin parts include dyes and fragrances to impart the color and smell of the fruit being imitated. The core or meat part may include moisturizers or lotions or other ingredients found in soaps. The skin functions to seal the fragrances and moisturizers in the soap core during storage and display. As a result, the composite article can be displayed and sold having the appearance of a fruit or vegetable and without significant release of fragrance or moisturizer. This same composite article can then be opened ("peeled") by the consumer in an enclosed space such as a bathroom, and immediately begin releasing fragrance. The product can contain excess moisturizer without fear of leakage, and can give a superior silky feel to the skin.

The product may be provided in loose or loosely-adhered slices, such as slices of oranges (with peel attached to each slice), or slices through a banana, with enough soap provided in each slice for a one-time use or for several washings, depending upon the size of the slice, that is, an amount may be sufficient for one or more baths.

The product is preferably produced by forming a core, dipping the core into a formulation that produces a sponge upon drying and foaming or blowing. The coating may be fused or mechanically bonded to the soap and may remain in place on the soap as the soap is being used. The coating forms a sponge that is not hidden and is thus is immediately available for mechanical rubbing of the skin.

The product thus provides a novel combination soap and sponge article which provides a unique bathing experience—it gives the aromatic, visual and tactile luxurious experience of washing the skin with a slice of fruit.

The foregoing has outlined rather broadly the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

For a fuller understanding of the nature and objects of the present invention reference should be made by the following detailed description taken in with the accompanying drawings in which:

FIG. 1A shows a partial sectional view of the soap core prior to coating, FIG. 1B corresponds to FIG. 1A and shows the soap core coated with foamable polymer, and FIG. 1C shows the final product with foamed polymer skin.

FIG. 2A shows a partial sectional foamed skin defining an internal cavity, and FIG. 2B corresponds to FIG. 2A but shows the internal cavity filled with soap.

DETAILED DESCRIPTION OF THE INVENTION

The present invention does not employ novel starting materials. The present invention is characterized by combining known starting materials in a novel way to form a novel end product that is considered revolutionary in the soap art.

The composite soap articles of the present invention comprise two main components: the soap core, which is formulated to mimic the meat of a fruit such as orange, tangerine, passion fruit, banana, or even pieces of pineapple or coconut, and the sponge skin, which is designed to mimic the skin appropriate to the fruit and, at the same time, serve as a wrapper for the soap and/or provide a sponge for mechanical washing of skin.

The core material is preferably a conventional soap material, but may be any solid or semi-solid formulation which can mimic the meat of a fruit and be solubilized in water, and may be, for example, a body gel, a solid shampoo, a suntan lotion, etc. The chemical processes by which solid soap and other solid cosmetic materials are made are well known in the art. Examples of suitable soaps are the sodium and potassium salts of lauric, myristic, palmitic, oleic and stearic acids and mixtures thereof. While the present invention is in no way limited to any type of solid soap or cosmetic composition, preferred soaps are the sodium and mixed sodium and potassium salts of fatty acids derived from coconut oil and tallow, which has been hydrogenated to an I.V. of from about 18 to about 40. Preferred soap compositions herein are those wherein the soap portion of the composition comprises from about 20% to about 50% soaps of coconut fatty acids and from about 50% to about 80% soaps of hydrogenated tallow fatty acids. Glycerin soaps are usually transparent and are preferred for aesthetics as well as mildness.

Sponge material may be provided to cover part or all of the soap core, and two or more materials may be provided covering different parts of the soap core or covering each other, but the foamed layer is always provided as a skin, and it is the foamed skin which characterizes the present invention.

In accordance with the present invention it is possible to form either the core first or the skin first.

Figure 1A:
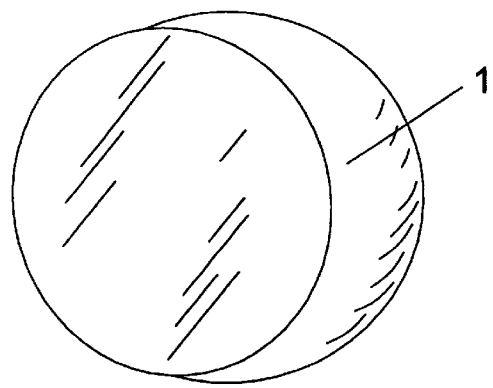
FIGS. 1A–C show a process for making a combination soap and sponge article according to the present invention.
Figure 1B:
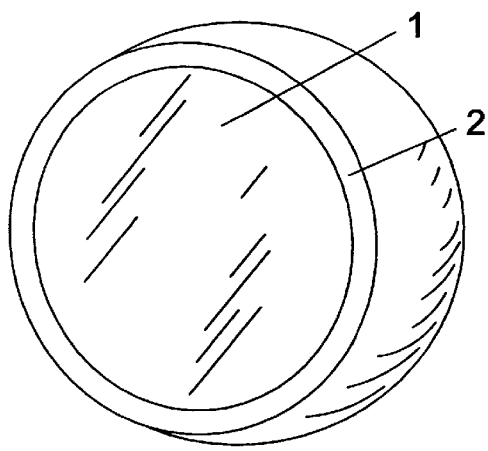
Figure 1C:
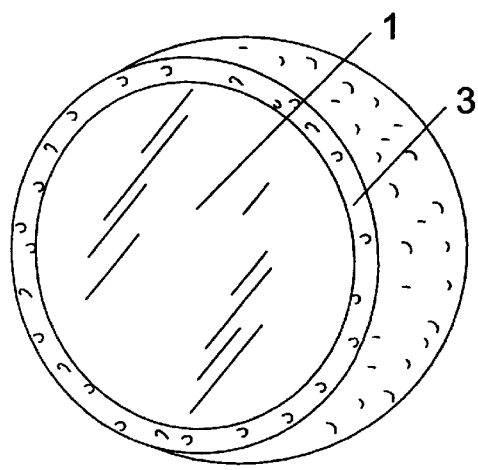

FIGS. 1A–C illustrate the case of forming the core first. Glycerin soap obtained from a commercial source is melted, fragrance and dyes are added, and the product is then poured into a suitable mold and allowed to cool. The soap core 1 resembles the meat of an orange with peel removed.

The soap core 1 is dipped into a mixture of a polyurethane pre-polymer and toluene diisocyanate and is coated 2 and allowed to air dry. The formation of carbon dioxide in situ provides for an uneven, bumpy coating 3 which imitates that of real fruit.

Figure 2A:
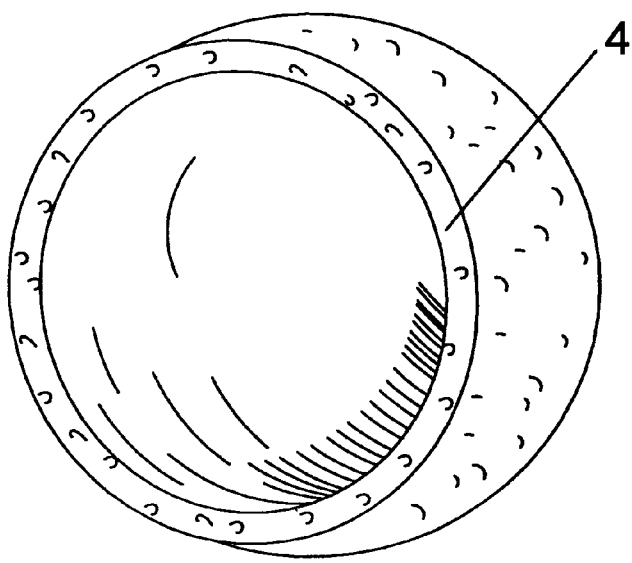
FIGS. 2A–B show an alternative process for making a combination soap and sponge article according to the present invention.
Figure 2B:
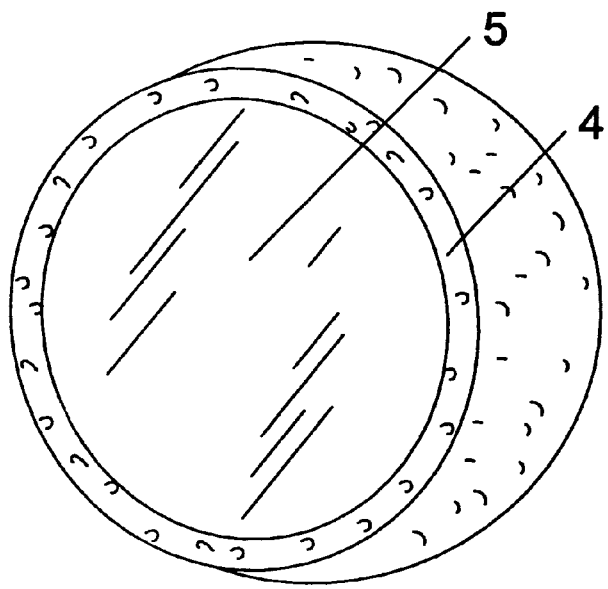

FIGS. 2A–B illustrate the case of forming the shell first. A PVA shell 4 is formed in a mold and hardened, and then liquefied soap is injected into the shell to form the soap core 5.

Exemplary soaps and sponges will now be discussed in grater detail.

Glycerin Soap

Any kind of solid soap may be used in accordance with the present invention, but glycerin soaps are preferred. Vegetable glycerin is a humectant that moisturizes the skin. Glycerin is also used to impart translucency to the soap. Glycerin soap can be obtained commercially, or it can be made by melting together clean shaved soap, strong (70–99%) alcohol (even vodka), and glycerin.

Glycerin soap made of pure vegetable soap with moisturizers and enriched with aloe vera and vitamin E is available from hobby shops ready for hobbyists to melt and mold. The soap comes in small cubes that can be heated to 71° C. (160° F.) on the stovetop or in a microwave. Color and fragrance are added to the molten soap, and the liquid is poured into a mold, cooled, and released. Suitable dyes and fragrances are also widely available.

Ready-to-use glycerin soap with orange—cantaloupe fragrance, with dewberry—blackcurrant fragrance, and with green apple fragrance is available from Prim & Proper, 214 West Main Street, Visalia, Calif.

Processes for commercial scale production of glycerin soaps are disclosed for example in U.S. Pat. No. 4,879,063 (Wood-Rethwill, et al.), the disclosure of which is incorporated herein by reference. This patent discloses a continuous, high-speed process for making translucent soap bars. The process uses a mixture of tallow and coconut fatty acids saponified with a mixture of sodium hydroxide and potassium hydroxide. To the neat soap is added a superfatting agent and glycerin and the resulting neat soap is dried to a moisture level of from about 14% to about 18%. The dried soap is thereafter subject to amalgamation where a slurry containing additional glycerin and a polyethylene glycol of molecular weight of about 600 is added to and mixed with said soap. Following amalgamation, the soap is refined and thereafter compacted and extruded into a continuous log which may be cut and stamped into bars.

Further, U.S. Pat. No. 4,405,492 (Nyquist, et al.) entitled "Process for making high-glycerin soap bars" teaches a process for making glycerinated toilet bar compositions which are substantially free of hard specks, wherein the soap is worked (e.g., milled) prior to the addition of glycerin.

Additional teaching relating to transparent soaps can be found in, e.g., H. Goldschmeidt, "Transparent Soaps", Soap/Cosmetics/Chemical Specialties, June 1972, pp. 37–38; G. R. Whalley, "Transparent Soaps", Perfumes & Essential Oil Record, July 1967, pp. 465–468; E. T. Webb, "Transparent Soaps", Soap Perfumery, Cosmetics, August 1958, pp. 770–772; J. V. Wells, "Transparent Soaps", Soap and Chemical Specialties, June 1955, pp. 39–41, July 1955, pp. 43–46 & 114; E. T. Webb, "Transparent Soap", American Perfumes and Cosmetics, vol. 82, April 1967, pp. 41–44; and "Transparent Soap Bars-Past and Present", Soap/Chemical Specialties, October 1967, pp. 102, 104, 106, 114–115.

The glycerin soaps of the present invention preferably contain from about 2% to about 25% glycerin, more preferably from about 5% to about 15% glycerin.

Other Soaps

Soaps other than glycerin soaps may be used, and preferred among these are the transparent soaps. Soaps which are clear have a certain aesthetic appeal to consumers. Often consumers associate clarity with "naturalness" which is a sought after benefit.

Bars of varying clarity, form and other physical properties have been described in the literature. Methods of manufacture are numerous and varied.

One of the earliest patents in the area is that of U.S. Pat. No. 2,820,768 (Fromont) which describes a transparent, substantially non-alkaline soap formed from a mixture of alkali metal soap and the reaction product between a free fatty acid and triethanolamine. The components are mixed together under heating at 100°–120° C. to obtain a homogeneous clear mass which is maintained upon cooling. This mass is poured into frames, cooled, cut and pressed into cakes or bars. Fromont is the basis for the bar product known as "Neutrogena".

U.S. Pat. No. 5,041,234 (Instone et al.) describes bars of high soap content that include a solvent system of water, triethanolamine and polyols. U.S. Pat. No. 3,793,214 and U.S. Pat. No. 3,926,828, both to O'Neill, describe utilizing mixtures of alkaline sodium compounds and alkanolamines to neutralize free fatty acids to obtain a glossy surface appearance even after repeated use of the product.

Japanese Patent 61/155499 (Hara) formulates amino acids in place of alkanolamines to achieve similar fast drying times but with the added benefits of good lathering and the avoidance of stickiness resulting from hygroscopicity. U.S. Pat. No. 4,206,069 (Borrello) overcomes the surface stickiness problem through careful selection of soap, detergent and solvent concentrations. U.S. Pat. No. 4,988,453 and U.S. Pat. No. 5,002,685, each assigned to Chambers et al., disclose translucent detergent bars based on a composition of soap, mono- and dihydric alcohols and water. Sugars (i.e. sucrose, fructose or glucose), cyclic polyols (i.e. glycerol, sorbitol or mannitol) and polyalkylene glycols were found useful as further components.

Several patents advocate special additives. U.S. Pat. No. 4,493,786 (Joshi) details use of lanolin and lanolin derivatives for inhibiting crystallization of soap thereby promoting clarity. U.S. Pat. No. 4,468,338 (Lindberg) fortifies a bar with sulfites to prevent progressive darkening upon storage. U.S. Pat. No. 4,741,854 (Krupa et al.) inhibits discoloration through a combination of sulfite and hydride compounds. U.S. Pat. No. 3,969,259 (Lages) is based on the discovery that germicide could be incorporated into a milled transparent soap without any opacifying effect. The germicide must, however, be first dissolved in a perfume material. The perfume solution is then added to the composition at any point between drying of the soap chips and extrusion thereof through a plodder.

In addition to transparent soaps, it is possible to use non-transparent soaps where the fruit or vegetable being imitated is opaque. Examples include banana, coconut, etc.

Sponge Forming Polymers

Many different types of sponge forming materials are known. Cellulose sponges are in wide use for many cleaning applications. The process for providing cellulose sponges is environmentally disadvantageous due to toxic gaseous and liquid by-products. The sponge is preferably made of a synthetic polymer, and may be polyurethane, polyester, polyethylene (e.g., metallocene polyethylene), polyether, polyester based urethane, base urethane, polyvinyl alcohol, and polyolefins such as polypropylene, silicate foams, ceramic foams, latex foams, and natural rubber foams and cellulose sponges.

The sponge forming polymers used in the present invention preferably produce sponges characterized by high elasticity, good tensile strength, high water absorbency, non-lint or particle producing, chemical inertness, softness, springback, pliability, good compressibility, smoothness, ability to retain a structural memory, a porous, open-cellular mass capable of absorbing liquids, and elasticity and flexibility when damp.

The polymers preferably provide a sponge which chemically or mechanically fuses with the soap to which it is coated, and does not excessively expand when wet or shrink when dry.

In the case that the soap core is formed first, it is preferred that the polymers have sufficient viscosity to form an even coat on the soap core by dipping, remain coated on the soap during the curing process, and can be foamed and cured without excessive heat. A small amount of heat may be advantageous to melt the outer sheen of the soap core and thus help to fuse the sponge and soap. However, excessive heat could melt the soap and deform the product. It is preferred that the foaming and curing is conducted rapidly so that only the outer skin is heated and foamed, with the soap core remaining below its melting point. It is also possible to chill the soap prior to coating and foaming/curing, thereby providing thermal protection to the soap core.

Foaming and curing may be conducted at about 150° C. or less, preferably at about 100° C. or less, most preferably between 20° C. and 40° C., for about 1 to about 10 minutes, although the temperature and time is selected depending on the shape and property of the product to be prepared. The preferred polymer provides for easy foaming and curing at room temperature within 1–5 minutes. Of course, in the case that a hollow foamed skin is formed first and this shell is subsequently filled with soap, there is no concern of temperature effecting the soap core, thus any conditions of temperature and time may be used for forming the skin.

Specific and non-limiting examples of some of the above foamed skin-forming materials will now be discussed in greater detail.

Polyvinyl Alcohol (PVA) Sponges

The PVA sponge may be a microporous material made from a hydroxylated polyvinyl alcohol polymer whose degree of polymerization is in a range of 1700 to 2500, and preferably between 1700 and 1800, and molecular weights of 75,000 to 120,000, preferably between 75,000 and 85,000.

The formation of a graft copolymer with other monomers modifies the physical properties of the microporous sponge, as well as to act as crosslinking agents. The crosslinking of Polyvinyl Alcohol, in the presence of a strong acid with such monomers as 1, 3, 5, 7, Tetraazatricyclo (3.3.1.13, 7) Decane, Pentaerythrite, alpha, trioxymethylene (meta formaldehyde), Methanol, or 2-Furaldehyde, produces a wide spectrum of physical properties which control hydrophilicity, softness or hardness, flexibility, and other parameters as described above.

Open-pore shaped articles of polyvinyl alcohol acetal sponge are usually prepared by foaming with air or with other gases in a process which consists in submitting a foam prepared of a polyvinyl alcohol solution to acetalization with an aldehyde in the presence of mineral acid, and subsequently washing the excess acid and aldehyde out of the foam rendered water-insoluble.

Another sponge forming polymer and process is disclosed in U.S. Pat. No. 4,083,906 (Schindler, et al.) entitled "Process for the manufacture of open-pore shaped articles of polyvinyl alcohol-acetal sponge". Schindler et al teach that starch products which were hitherto used as pore-forming substances in the manufacture of polyvinyl alcohol acetal sponges can be replaced by polyethylene glycol or polyacrylamide. This results in a more uniform distribution of pore size, lower shrinkage of the sponge material during the acetalization, and easier washing of the sponge after the acetalization.

Silicone Rubber Sponges

Silicone rubber sponges are generally manufactured by adding a crosslinking agent, foaming agent, or the like to a silicone rubber compound, milling the mixture, and then extruding the mixture through an extruder whereupon it is foamed and cured in a continuous line by way of atmospheric hot air vulcanization (HAV) or other conventional processes. Commonly used crosslinking agents include acyl peroxides such as benzoyl peroxide, 2,4-dichlorobenzoyl peroxide, p-chlorobenzoyl peroxide, and p-methylbenzoyl peroxide, alone or combined with other peroxides such as dicumyl peroxide, 2,5-dimethylbis(2,5-tert-butyl peroxy) hexane, ditert-butyl peroxide, and tert-butyl perbenzoate. Included in the foaming agents are azobisisobutyronitrile, dinitropentamethylenetetramine, p,p'-oxybis (benzenesulfonyl hydrazide), N,N'-dinitroso-N,N'-dimethylterephthalamide, and azodicarbonamide.

From a safety and hygienic aspect care should be taken to ensure non-use of foaming agents like azobisisobutyronitrile and dinitropentamethylenetetramine which leave decomposition residues which are detrimental to the human body. Also, acyl peroxide cross-linking agents such as benzoyl peroxide, 2,4-dichlorobenzoyl peroxide, p-methylbenzoyl peroxide leave decomposition residues which are more or less detrimental to the human body. Formation of such decomposition residues is undesirable for the maintenance of a working environment, and removal of decomposition residues requires a long term of heating.

Thus, as preferred foaming agents, azodicarbonamide and p,p'-oxybis(benzenesulfonyl hydrazide) are known to have minimal influence on the human body. It is also known that hygienically most preferred sponges are formed by crosslinking through platinum-catalyzed addition reaction between alkenyl and SiH groups. It is thus desired to produce silicone rubber sponges by using these foaming agents and the addition curing reaction route.

Preparation of silicone rubber sponges by way of addition reaction is disclosed in Japanese Patent Publication (JP-B) No. 43294/1972. JP-B 1459/1978 discloses a process for foaming and curing a silicone compound while partially effecting addition reaction. The latter process requires an extra step of aging for allowing addition reaction to take place partially.

Japanese Patent Application Kokai (JP-A) No. 223034/1986 discloses a polydiorganosiloxane based sponge which is prepared from a composition comprising a vinyl-containing polydimethyl-siloxane, a liquid foaming agent which is gaseous at 25° C. under atmospheric pressure, and a platinum or rhodium catalyst. The polydimethylsiloxane composition is cured through catalytic hydrosilation and foamed at the same time. The liquid foaming agent is, however, difficult to handle and expensive.

JP-B 10180/1988 discloses a foamable silicone rubber composition comprising a polydiorganosiloxane having a viscosity of up to 100,000 centistokes, a polyorganohydrogensiloxane, and p,p'-oxybis (benzenesulfonyl hydrozide) as a foaming agent. A platinum catalyst catalyzes the addition reaction between an alkenyl group of the polydiorganosiloxane and a SiH group of the polyorganohydrogensiloxane. This curing, coupled with concurrent foaming, results in a sponge.

U.S. Pat. No. 5,214,074 (Takahashi et al.) entitled "Foamable silicone rubber composition and silicone rubber sponge", the disclosure of which is incorporated herein by reference, teaches the foaming and curing, preferably through microwave (UHF) vulcanization, into silicone rubber sponge, of a foamable silicone rubber composition comprising (A) a diorganopolysiloxane having a viscosity of at least $10^6$ cs at 25° C., (B) an organohydrogenpolysiloxane, (C) a platinum catalyst, (D) azodicarbonamide foaming agent, and (E) an acetylenic alcohol reaction controlling agent. The sponge having satisfactory strength and foam properties is obtained, which is also safe for contact with human skin.

On curing the composition, the addition reaction control agent such as an acetylenic alcohol is effective for controlling the rate of addition curing reaction so as to match with the rate of decomposition of the foaming agent, making it possible to cure and foam a high viscosity polymer in the form of diorganopolysiloxane having a viscosity of at least $10^6$ cs into a silicone rubber sponge. Silicone rubber sponges having improved strength and cell structure can be produced without aging.

The silicone rubber composition may be obtained by uniformly mixing the above-mentioned components in a conventional rubber masticating machine such as twin roll mill, Banbury mixer, and dough mixer or kneader and optional heat treatment. The order of mixing the components is not critical. One effective sequence of mixing is by first masticating components (A) and (F) uniformly and successively mixing components (C), (E), (D), and (B) in this order. The resulting silicone rubber composition may be molded into a silicone rubber sponge form in a conventional manner by conventional molding methods including casting, pressure molding in molds, extrusion molding, and coating to various substrates. Then, after being coated onto the soap core, the composition is expanded by any of the conventional foaming methods including atmospheric hot air vulcanization (HAV), steam continuous vulcanization (CV), molten salt vulcanization (LCM), and microwave irradiation vulcanization (UHF vulcanization).

Foaming and curing may be conducted at about 100° C., preferably at about 150° C. or less, for about 1 to about 20 minutes, although the temperature and time is selected depending on the shape and property of the product to be prepared. It is preferred that the foaming and curing is conducted rapidly so that only the outer skin is heated and foamed, with the soap core remaining below its melting point. It is also possible to chill the soap prior to coating and foaming/curing, thereby providing thermal protection to the soap core.

After the foaming and curing step, if desired, the silicone sponge is post-cured, completing vulcanization and decomposition of the foaming agent.

Polyurethane Sponges

Polyurethane sponge materials have been known and utilized for a long time. Most of these sponges are synthesized from isocyanate terminated polyethyleneoxide, polypropyleneoxide, polyesters, or combinations thereof. Coreactants are usually polyols or polyamines of similar polymeric backbones. Water is also used as a coreactant which generates a blowing agent (i.e. carbon dioxide) in addition to generating a crosslinked system. The majority of these materials produce a sponge material with little hydrophilic character (moderate bulk hydrophilicity, but poor surface properties), and few of the characteristics associated with a cellulose sponge. Materials which are indicated to be hydrophilic usually contain a sacrificial hydrophilic compound or have excessive swell (in excess of 50%).

Isocyanate terminated sulfopolyethyleneoxide prepolymers for foam applications are described in U.S. Pat. No. 3,988,268. The use of sulfonated urethanes have otherwise been mainly restricted to the synthesis of water-soluble or water-dispersible materials, e.g. U.K. Pat. No. 1,483,687. Prepolymers based on isocyanate-terminated polyethyleneoxide are described in U.S. Pat. Nos. 4,160,076; 4,384,050; 4,384,051; and 4,377,645.

Coloring Agent

A coloring agent, preferably a water-soluble coloring agent, may be added to both the soap and the sponge forming polymer for imparting color to the final product, and examples of colorants include Food, Drug and Cosmetic Agency approved colors. It is generally preferred to use small amounts of dyes, and to use dyes which do not react with skin or hair.

Fragrance

Substances used to produce a desired fragrance may be any one or more of those which are commonly used by those skilled in the art of toiletry fragrance chemistry or perfumery, some of which are listed in the following texts: Robert R. Calkin, J. Stephan Jellinek, *Perfumery, Practice and Principle*, John Wiley and Sons, Inc., New York, 1994; Rudiger Hall, Dieter Klemme, Jurgen Nienhaus, *Guide to Fragrance Ingredients*, H&R Edition, R. Gross & Co. Publishing, Hamburg, 1985; Julia Muller, *The H&R Book of Perfume*, H&R Edition, Johnson Publications, Ltd., London, 1984; *Fragrance Guide-Feminine Notes*, Masculine Notes, H&R Edition, R. Gross & Co. Publishing, Hamburg, 1985 which are incorporated by reference herein. It is specifically intended that the present invention not be limited to any particular fragrance or combination of fragrances, whether known or discovered in the future since any fragrance or chemical substances which humans find pleasant and desirable to inhale are within the scope of the present invention.

It is however preferred in accordance with the present invention that the fragrance is consistent with the inventive concept of providing a soap which mimics the feel, appearance and fragrance of a natural fruit.

The amount of fragrance substance (e.g., perfume base) included in the composition may vary, and the amount of the fragrance substance may comprise from 0.01 to 10% by weight of the total cosmetic or cleansing composition as well as of the sponge forming polymer, with about 0.5% to about 3% being preferred. Quantities of fragrance outside of this preferred range may also be used, including significantly larger amounts.

Examples of fragrances include the following:

Allspice (*Pimenta dioica*)
Chamomile, German (*Matricaria recutita*, formerly *M. chamomilla*)
Chamomile, Roman (*Chamaemelum nobile*, formerly *Anthemis nobilis*)
English Chamomile (*Anthemis nobilis*)
Cinnamon (*Cinnamomum zeylanicum*)
Coriander (*Coriandrum sativum*)
Eucalyptus (*Eucalyptus globulus*)
Eucalyptus Australiana (*E. australiana*)
Lemon Eucalyptus (*E. citriodora*)
Dives or Broad-Leaved Peppermint (*E. dives*)

Peppermint Eucalyptus (*E. piperita*)
Jasmine (*Jasminum officinale* and *J. grandiflorum*)
Jasmine Sambac (*Jasminun officianalis sambac*)
Chinese Jasmine (*J. sambac*)
Lavender (*Lavandula angustifolia*, previously *L. vera* and *L. officinale*)
Lavandin (*L. x intermedia* or *L. x hybrida*)
Spike Lavender (*L. latifolia*)
Stoechas Lavender (*L. stoechas*)
Lemon (*Citrus limon*)
Cedro Oil
Lemongrass (*Cymbopogon citratus*)
Palmarosa (*C. martini*)
Petitgrain (*Citrus aurantium*)
Ravensara Aromatica (*Cinnamomum camphora*)
Lemongrass Cochin (*C. flexuosus*)
Citronella (*C. nardus*)
Java Citronella (*C. winterianus*)
Lovage (*Levisticum officinale*)
Lemon Verbena (*Aloysia triphylla*, formerly *Lippia citriodora*)
Mimosa (*Acacia decurrens* var. *dealbata*)
Myrtle (*Myrtus communis*)
Orange (*Citrus sinensis, Citrus aurantium*)
Neroli (*Citrus aurantium*)
Bergamot (*Citrus bergamia*)
Neroli sur Petitgrain (*Citrus aurantiumflowers*)
Bitter Orange (*C. aurantium* var. *amara*)
Grapefruit (*C. x paradisi*)
Mandarine (*Citrus nobilis*)
Tangerine (*Citrus reticulata*)
Pink Grapefruit (*Citrus paradisii*)
Lime (*C. aurantiifolia*)
Tangerine or Mandarin (*C. reticulata*)
Orange Blossom (*Neroli, Citrus aurantium* var. *amara*)
Peppermint (*Mentha piperita*)
Rose (*Rosa damascena, R. gallica*, and others)
Rose Otto (*Rosa damascena*)
Cabbage Rose (*R. centifolia*)
Rosemary (*Rosmarinus officinalis*)
Rosmarinus Pyramidalis (*R. pyramidalis*)
Rosewood (*Aniba rosaeodora*)
Sage (*Salvia officinalis*)
Spanish Sage (*S. lavandulaefolia*)
Sandalwood (*Santalum album*)
Spearmint (*Mentha Spicata*)
Vanilla (*Vanilla planifolia*)
Violet (*Viola odorata*)

Process of Manufacture

In accordance with a first embodiment of the invention, the soap core first is produced by melting a glycerin soap, adding orange fragrances and dyes to the molten soap, pouring the molten soap into an orange shaped mold, cooling, and removing the soap.

The same dyes and fragrances may added to the sponge forming composition. Any coating process may be used to coat the sponge forming polymerzable composition onto the soap core, but simple dipping is preferred.

The coating is foamed and cured (usually simultaneously) to produce a sponge skin fused to the orange soap core. The orange imitating composite article may be employed as-is, with the protective skin to be peeled off from the soap core by the consumer prior to use, or with the foamed skin being left on the soap core and being used as a sponge in the bathing or showering process. Alternatively, the composite article can be sectioned, e.g., into orange wedges which may be loosely adhered to each other. The soap core may contain release agents to prevent sticking of orange sections, or release agents may be coated onto the orange wedges at the time of slicing, to prevent re-adhesion.

The product produced in this example resembles an orange in appearance, color and fragrance. To use, one of the orange wedges may be simply pulled from the orange, and the sponge-soap composite article can then be used in the conventional way. The residual orange with one or more slices removed makes an attractive display in a bathroom and imparts a fresh citrus aroma to the bathroom.

EXAMPLE 1

"Orange" Glycerin Soap

Glycerin soap obtained from Surrey Inc. is melted, orange fragrances and dyes are added to the molten soap, the molten soap is poured into an orange core shaped mold, cooled, and removed. More specifically, the following materials and procedures were employed.

| Item | % | Ingredient | Supplier |
| --- | --- | --- | --- |
| 1. | q.s. | Meltable glycerin soap base | SURREY |
| 2. | 1.00 | Dragoderm (Unhydolyzed Wheat Protein) | Dragoco |
| 3. | 0.30 | Farnesol (3,7,11-trimethyldodeca-2,6,10-trienol) | Dragoco |
| 4. | TBD | DRAGOCO Fragrance 0/723188 | Dragoco |
| 5. | 0.20 | FD&C Yellow # 6 @ 1.0% | |
| | 100.0 | Total | |

The glycerin soap was melted in a large vessel at 65° C. The molten soap was cooled to 50° C. and ingredients 2, 3 and 5 were added. The batch was cooled to 40° C. and the amount of fragrance oil to produce a suitable fragrance intensity was added, usually 2–5%. The product was then poured into a suitable mold and allowed to cool.

EXAMPLE 2

"Grapefruit" Glycerin Soap

| Item | % | Ingredient | Supplier |
| --- | --- | --- | --- |
| 1. | q.s. | Meltable glycerin soap base | SURREY |
| 2. | 1.00 | Dragoderm (Unhydolyzed Wheat Protein) | Dragoco |
| 3. | 0.30 | Farnesol (3,7,11-trimethyldodeca-2,6,10-trienol) | Dragoco |
| 4. | TBD | DRAGOCO Fragrance 0/723186 | Dragoco |
| 5. | 0.20 | FD&C Red # 33 @ 0.1% | |
| 6. | 0.10 | FD&C Red # 4 @ 0.5% | |
| | 100.0 | Total | |

The glycerin soap was melted in a large vessel at 65° C. The molten soap was cooled to 50° C. and ingredients 2, 3, 5 and 6 were added. The batch was cooled to 40° C. and the amount of fragrance oil to produce a suitable fragrance intensity was added, usually 2–5%. The product was then poured into a suitable mold and allowed to cool.

EXAMPLE 3
"Orange" Polyurethane Foam Skin

| Item | % | Ingredient | Supplier |
|---|---|---|---|
| 1. | 37.30 | Deionized Water | |
| 2. | 0.05 | Kathon CG(Preservative) | Rohm & Haas |
| 3. | 0.65 | Yellow # 6 @ 1.0% | |
| 4. | 60.00 | Hypol 3000(Polyurethane Pre-polymer, Monomer Toluene Diisocyanate) | Dow Chemical |
| 5. | 2.00 | DRAGOCO Fragrance 0/723188 | Dragoco |
| | 100.00 | Total | |

In a large vessel ingredients 1–3 were mixed by hand until uniform. The remaining ingredients were added and mixed until homogeneous. At this point the solution began to rise due to the formation of carbon dioxide. The glycerin soap was then dipped and coated and allowed to air dry. The formation of carbon dioxide in situ provided for an uneven, bumpy coating which imitated that of real fruit skin.

EXAMPLE 4
"Grapefruit" Polyurethane Foam Skin

| Item | % | Ingredient | Supplier |
|---|---|---|---|
| 1. | 37.30 | Deionized Water | |
| 2. | 0.05 | Kathon CG(Preservative) | Rohm & Haas |
| 3. | 0.48 | FD&C Yellow # 5 @ 0.1% | |
| 4. | 0.15 | FD&C Red # 33 @ 0.1% | |
| 5. | 0.03 | FD&C Red # 4 @ 0.5% | |
| 6. | 60.00 | Hypol 3000(Polyurethane Pre-polymer, Monomer Toluene Diisocyanate) | Dow Chemical |
| 7. | 2.00 | DRAGOCO Fragrance 0/723186 | Dragoco |
| | 100.00 | Total | |

In a large vessel ingredients 1–4 were mixed by hand until uniform. The remaining ingredients were added and mixed until homogeneous. At this point the solution began to rise due to the formation of carbon dioxide. The glycerin soap was then dipped and coated and allowed to air dry. The formation of carbon dioxide in situ provided for an uneven, bumpy coating which imitated that of real fruit skin.

EXAMPLE 5
"Orange" PVA Sponge Shell/Glycerin Core

The following example illustrates the second embodiment of the invention, wherein the shell is formed prior to forming the core.

One hundred thirty five grams of polyvinyl alcohol having a degree of polymerization of approximately 1700 to 2500, is slowly added with stirring to 1000 ml of water. The slurry that is produced is then cooked at 93° C. until all of the polyvinyl alcohol goes into solution. A surfactant is added, which is preferably nonionic, though other surfactants and combinations thereof can be used to modify the cell structure and its properties. The solution is cooled to room temperature, with the aid of slow mechanical stirring, and a solution containing 32 grams of 1,3,5,7-tetraazatricyclo (3.3.1.13,7) decane is added slowly till thoroughly dispersed. With the aid of a high speed high shear mechanical stirrer, capable of aerating this mixture, the solution is vigorously frothed and whipped till a rise of 2.5:1 is observed in the foam and froth volume. One hundred ml of 30% sulfuric acid is slowly added after the froth rise reaches 2.5:1. This acid catalyst is rapidly stirred for 60 sec. or less, till thoroughly dispersed into the polyvinyl alcohol mixture. The resulting mixture of polyvinyl alcohol, cross linking agent and acid catalyst is used to coat the internal wall of a mold having an orange-shaped cavity, and allowed to cure, forming a 2–4 mm thick shell. The mixture is cured at 43° C.–49° C. for 10 hours. The resulting sponge is a microporous, soft, reticulated matrix of cross linked polyvinyl alcohol.

The glycerin soap prepared in Example 1 is liquefied, injected into the hollow sponge shell, and cooled to room temperature, forming a product which resembles an orange in appearance, color, and fragrance. The molten soap partially impregnates the sponge shell, thus forming excellent adherance. The orange is sliced into wedges with a wire blade and the sections are coated with release agent.

To use, one of the orange wedges is simply pulled from the orange, and the sponge-soap composite article is used in the conventional way. The residual orange with slices removed makes an attractive display in a bathroom and imparts a fresh citrus fragrance to the bathroom.

Although this invention has been described in its preferred form with a certain degree of particularity with respect to a solid foam product comprising a hydrophilic-hygroscopic hydrogel polymer which contains within its matrices various hand soap cleansing compositions, it is understood that the present disclosure of the preferred form has been made only by way of example, and that numerous changes in the details of structures and composition of the product may be resorted to without departing from the spirit and scope of the invention.

What is claimed is:

1. A solid cosmetic formulation and foamed polymer skin composite article comprising:
   a solid cosmetic formulation core having the shape, color and fragrance of a fruit or vegetable with skin removed; and
   a foamed polymer skin having an outer surface having the shape and color of the corresponding skin of the fruit or vegetable, said foamed polymer being intimately chemically or structurally fused to said core.

2. A solid cosmetic formulation and foamed polymer composite article as in claim 1, wherein said solid cosmetic formulation is a soap, a solid body gel, a solid shampoo, or a solidified suntan lotion.

3. A solid cosmetic formulation and foamed polymer composite article as in claim 2, wherein said soap is a glycerin soap.

4. A solid cosmetic formulation and foamed polymer composite article as in claim 3, wherein said glycerin soap is transparent or translucent.

5. A solid cosmetic formulation and foamed polymer composite article as in claim 1, wherein said foamed polymer substantially completely covers said solid cosmetic formulation core.

6. A solid cosmetic formulation and foamed polymer composite article as in claim 1, wherein said foamed polymer is a sponge selected from the group consisting of (a) cellulose sponges, (b) sponges formed of synthetic polymers selected from the group consisting of polyurethane, polyester, polyethylene, polyether, polyester based urethane, polyvinyl alcohol, (c) sponges formed from polyolefins, (d) silicate foams, (e) ceramic foams, (f) latex foams, and (e) natural rubber foams.

7. A solid cosmetic formulation and foamed polymer composite article as in claim 1, wherein said composite article is sliced into smaller pieces, which pieces are loosely adhered to form a pull-apart article.

8. A solid cosmetic formulation and foamed polymer composite article as in claim 1, wherein said composite article has the appearance and fragrance of whole or sliced grapefruit, orange, tangerine, passion fruit, pineapple, banana, coconut.

9. A solid cosmetic formulation and foamed polymer composite article as in claim 1, wherein said foamed polymer has the same fragrance as the core material.

10. A soap and sponge composite article produced by a process comprising:

forming a glycerin soap core having the shape, color and fragrance of a fruit or vegetable with skin removed;

coating a foamable polymerizable composition onto said glycerin core; and foaming and curing the polymerizable composition to form a sponge skin having the shape and color of the corresponding skin of said fruit or vegetable;

wherein foaming may take place prior to or subsequent to coating.

11. A soap and sponge composite article as in claim 10, wherein said soap is a glycerin soap.

12. A soap and sponge composite article as in claim 11, wherein said glycerin soap is transparent or translucent.

13. A soap and foamed polymer composite article produced by a process comprising:

forming a shell comprising a foamed polymer defining a cavity;

introducing liquefied soap into said cavity and hardening said soap to form a soap core within said foamed polymer shell, wherein said composite article has the shape, color and fragrance of a fruit or vegetable.

14. A soap and sponge composite article as in claim 13, wherein said soap is a glycerin soap.

15. A soap and sponge composite article as in claim 14, wherein said glycerin soap is transparent or translucent.

* * * * *